United States Patent
Taillefer et al.

(10) Patent No.: US 8,399,680 B2
(45) Date of Patent: Mar. 19, 2013

(54) ARYLAMINE SYNTHESIS METHOD

(75) Inventors: Marc Taillefer, Vailhauques (FR); Ning Xia, Montpellier (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 269 days.

(21) Appl. No.: 12/680,606

(22) PCT Filed: Sep. 24, 2008

(86) PCT No.: PCT/FR2008/051701
§ 371 (c)(1),
(2), (4) Date: Jul. 12, 2010

(87) PCT Pub. No.: WO2009/050366
PCT Pub. Date: Apr. 23, 2009

(65) Prior Publication Data
US 2010/0298571 A1  Nov. 25, 2010

(30) Foreign Application Priority Data
Sep. 28, 2007 (FR) .................................... 07 06827

(51) Int. Cl.
*C07D 213/73* (2006.01)
*C07C 209/00* (2006.01)

(52) U.S. Cl. ........................ 546/311; 564/395

(58) Field of Classification Search ........................ None
See application file for complete search history.

(56) References Cited

U.S. PATENT DOCUMENTS

| | | | |
|---|---|---|---|
| 1,840,760 | A | 1/1932 | Williams |
| 2,455,932 | A | 12/1948 | Hughes |
| 3,975,439 | A | 8/1976 | Klabunde |
| 2001/0047013 | A1 | 11/2001 | Lang et al. |
| 2005/0165256 | A1 | 7/2005 | Ismaili et al. |

FOREIGN PATENT DOCUMENTS

| | | |
|---|---|---|
| DE | 586879 | 10/1933 |
| EP | 0 549 263 A2 * | 12/1992 |
| EP | 0 549 263 | 6/1993 |
| WO | WO-03/006420 | 1/2003 |
| WO | WO-2004/052833 | 6/2004 |
| WO | WO2007/109365 | 9/2007 |

OTHER PUBLICATIONS

SparkNotes in Intro to Organic Chemistry4 downloaded from www.sparknotes.com/chemistry/organic4/intro/ accessed May 31, 2012.*
Shen et al, "Palladium-Catalyzed Coupling of Ammonia and Lithium Amide with Aryl Halides", 2006, pp. 10028-10029, vol. 128, J. Am. Chem. Soc.
Lang et al, "Amination of Aryl Halides Using Copper Catalysis", 2001, pp. 3251-3254, vol. 42, Tetrahedron Letters.

* cited by examiner

*Primary Examiner* — David K O'Dell
*Assistant Examiner* — Heidi Reese
(74) *Attorney, Agent, or Firm* — B. Aaron Schulman, Esq.; Stites & Harbison PLLC

(57) ABSTRACT

The invention relates to a method for preparing arylamines and, in particular, a method for preparing aniline and anilines substituted on the aromatic ring from ammonia, under easily-industrialized mild conditions with good selectivity and yields, in the presence of a catalytic system including a copper complex.

36 Claims, No Drawings

ARYLAMINE SYNTHESIS METHOD

The present invention relates to a process for the preparation of arylamines and in particular to a process for the preparation of aniline and anilines substituted on the aromatic ring system, starting from aqueous ammonia, under mild conditions which can be easily operated industrially, with good selectivities and good yields.

Aniline (or phenylamine) and its derivatives, which will be referred to in the present account under the generic term of arylamines, are compounds of major importance in organic synthesis, in particular as synthetic intermediates in numerous fields, including dyes, the pharmaceutical industry and the plant protection industry, and for the preparation of aromatic isocyanates.

Aniline is currently mainly synthesized by nitration of benzene, followed by catalytic hydrogenation of the nitrobenzene obtained. The synthesis is thus a two-stage synthesis which might advantageously be simplified, so as to reduce the production costs, while being relieved of certain toxic products, such as, for example, the metal catalysts used in the hydrogenation stage.

Furthermore, ammonia is an inorganic chemical compound with one of the greatest outputs in the world. It is mainly used in the production of fertilizers, explosives and nitrogenous organic compounds.

Ammonia might thus advantageously be used in the preparation of aniline and its derivatives. However, there currently exists only a few examples of catalytic coupling reactions which use ammonia as reactant.

The "Ullmann" reaction, which is catalyzed with copper, is one of the most widely used methods industrially due to the attractive cost of copper, in comparison with the cost of other noble metals, such as palladium, ruthenium and others. This reaction involves an aromatic compound carrying a leaving group with a nucleophilic compound carrying a heteroatom (such as the nitrogen atom) capable of replacing the leaving group, thus creating a carbon-heteroatom (for example, carbon-nitrogen) bond.

Recent studies illustrate the difficulties in using ammonia (gaseous ammonia or liquid ammonia, that is to say aqueous ammonia) as nitrogenous nucleophile, in the presence of an aromatic derivative and of a catalyst, in the preparation of aniline and aniline derivatives, according to the "Ullmann" reaction scheme.

For example, the document WO 2003/006420 and the publication by Hartwig et al. (*J. A. C. S.*, 128, (2006), 10028-9) provide reactions for the amination of aromatic derivatives with aqueous ammonia in the presence of palladium-based complexes as catalysts. These reactions are complex, are not very economic (use of expensive ligands and palladium) and are carried out under high pressures. Extrapolation to the industrial scale thus appears difficult to envisage.

Likewise, the operating conditions described in patent application WO 2004/052833 (temperatures: 200° C.; pressures: 69 to 90 bar) do not make the process very profitable on the industrial scale. In addition, the catalyst used is an expensive copper oxide/titanium dioxide pair and the reaction medium optionally comprises benzene, which is a toxic solvent.

Patent EP-B-1 511 726 for its part provides the amination of trichlorobenzene in the presence of copper iodide and of aqueous ammonia in an aqueous medium. However, this reaction is limited to a hyperactivated aromatic derivative and is carried out at high temperatures (180° C.) under high pressures (40 bar).

Lang et al. (*Tetrahedron Letters*, 42, (2001), 3251-3254 & US 2001/0047013) describe a process for the amination of aromatic halides by catalysis with copper. However, the brominated aromatic precursors are necessarily activated and the selectivities observed are low.

Thus, a first object of the present invention consists in providing a process for the preparation of arylamines which does not have the known disadvantages of the state of the art.

Another object of the present invention is to provide a process which makes possible the preparation of arylamines under mild conditions, that is to say at temperatures and pressures close to or relatively close to standard temperature and pressure conditions, and which is economic, which can be easily operated industrially and which is of low toxicity.

Yet another object consists in providing a process for the preparation of arylamines with high yields and high selectivities.

The present invention is targeted, as other object, at providing a process for the preparation of arylamines employing a catalyst which is nontoxic or of low toxicity, which is easy to prepare and which is of relatively low cost, sufficiently low to be profitable on the industrial scale.

The present invention is targeted, as other object, at providing a process for the preparation of arylamines which is easy to carry out, which can be easily operated industrially and which is suitable for a great variety of aromatic substrates, without major modification to the operating conditions, making possible the synthesis of arylamines of all types, for example unsubstituted (aniline) or substituted, or also comprising one or more unsubstituted aromatic rings (for example, aminonaphthalenes) or substituted aromatic rings.

Yet other objects will become apparent in the light of the description and examples which follow.

It has now been discovered that the objects defined above can be achieved, in all or in part, by virtue of the process of the present invention which is set out below.

Thus, a subject matter of the present invention is first of all a process for the preparation of arylamines of formula $R^0$—$(NH_2)_n$, where $R^0$ is an aromatic radical and n is between 1 and 3, said process comprising the following steps:

a) preparation of a reaction medium comprising:
    1) an aromatic compound carrying at least one leaving group, of formula $R^0$—$Y_m$, in which $R^0$ is an aromatic radical and Y is a leaving group, m being between 1 and 3;
    2) an aqueous ammonia solution;
    3) a catalytic system comprising a metal/ligand complex;
    4) optionally a base; and
    5) optionally a solvent;
  b) heating said reaction medium to a temperature of between 20° C. and 200° C.;
  c) carrying out the reaction; and
  d) extracting and isolating the arylamine $R^0$—$(NH_2)_n$ formed.

In a preferred embodiment, the metal is copper.
In another embodiment, the metal is iron.

In one embodiment, a subject matter of the present invention is a process as defined above in which the aromatic compound carrying a leaving group is a compound of formula $R^0$—Y, in which $R^0$ is an aromatic radical and Y is a leaving group.

The general scheme of the process according to the present invention can be illustrated as follows when n is equal to 1:

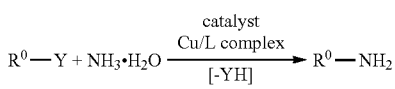

in which scheme R⁰—Y is an aromatic compound carrying a leaving group Y.

According to the process of the present invention, an arylation reaction is carried out by reacting an aromatic compound carrying at least one leaving group with an aqueous ammonia solution, that is to say a solution of ammonia gas dissolved in water.

In the account of the present invention which follows, the term "arylation" is used in its broad sense, since the use is envisaged of an aromatic compound carrying a leaving group which is either of aromatic carbocyclic type or of aromatic heterocyclic type.

More specifically, in the aromatic compound carrying a leaving group R⁰—Y, R⁰ is an aromatic or heteroaromatic radical comprising from 2 to 20 atoms which is monocyclic or polycyclic.

Y is a leaving group, preferably a halogen atom or a sulfonic ester group of formula —OSO$_2$—R$^e$, in which R$^e$ is a hydrocarbon radical.

In the formula of the above sulfonic ester group, R$^e$ is a hydrocarbon group of any nature. However, given that Y is a leaving group, it is advantageous from an economic viewpoint for R$^e$ to be simple in nature and to more particularly be a linear or branched alkyl radical having from 1 to 4 carbon atoms, preferably a methyl or ethyl group; however, it can also be, for example, a phenyl or tolyl group or a trifluoromethyl group.

Among the Y groups, the preferred group is a triflate group, which corresponds to an R$^e$ group being a trifluoromethyl group.

According to another aspect, the choice is preferably made, as preferred leaving groups, of a halogen atom, preferably bromine, chlorine or iodine.

According to a preferred embodiment of the invention, the aromatic compound carrying a leaving group R⁰—Y has the formula (A):

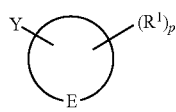

in which:

E symbolizes the residue of a ring forming all or part of a carbocyclic and/or heterocyclic system which is aromatic and monocyclic or polycyclic;

R¹, which are identical or different, are substituents on the ring;

Y is a leaving group as defined above; and p is the number of substituents on the ring.

The invention applies in particular to the haloaromatic compounds corresponding to the formula (A) in which E is the residue of an optionally substituted cyclic compound preferably having at least 5 atoms in the ring, preferably 5 or 6 atoms, and representing at least one of the following rings:

a monocyclic aromatic carbocycle or a polycyclic aromatic carbocycle, that is to say a compound consisting of at least 2 aromatic carbocycles which form, together, ortho- or ortho- and peri-fused systems or a compound consisting of at least 2 carbocycles, of which one is aromatic, which form, together, ortho- or ortho- and peri-fused systems;

a monocyclic aromatic heterocycle comprising at least one of the heteroatoms P, O, N and/or S or a polycyclic aromatic heterocycle, that is to say a compound consisting of at least 2 heterocycles comprising at least one heteroatom in each ring, at least one of the two rings of which is aromatic, which form, together, ortho- or ortho- and peri-fused systems; or a compound consisting of at least one carbocycle and at least one heterocycle, at least one of the rings of which is aromatic, which form, together, ortho- or ortho- and peri-fused systems.

More particularly, the optionally substituted residue E preferably is the residue of an aromatic carbocycle, such as benzene, of an aromatic bicycle comprising two aromatic carbocycles, such as naphthalene, or of a partially aromatic bicycle comprising two carbocycles, one of the two of which is aromatic, such as 1,2,3,4-tetrahydronaphthalene.

The invention also envisages the fact that E can be the residue of a heterocycle. Mention may be made, as specific examples, of an aromatic heterocycle, such as furan or pyridine; an aromatic bicycle comprising an aromatic carbocycle and an aromatic heterocycle, such as benzofuran or benzopyridine; a partially aromatic bicycle comprising an aromatic carbocycle and a heterocycle, such as methylenedioxy-benzene; an aromatic bicycle comprising two aromatic heterocycles, such as 1,8-naphthylpyridine; or a partially aromatic bicycle comprising a carbocycle and an aromatic heterocycle, such as 5,6,7,8-tetrahydroquinoline.

In the process of the invention, use is preferably made of a haloaromatic compound of formula (A) in which E is an aromatic ring system, preferably a benzene or a naphthalene ring system.

The aromatic compound of formula (A) can carry one or more substituents. In the present text, "more" is understood to mean generally less than 4 substituents, that is to say that, in the formula (A), n is 0, 1, 2, 3, 4 or 5, generally n is 0, 1, 2, 3 or 4 and preferably n is 0 or 1, and even 2.

The optional substituent(s) R¹ of the residue E is(are) of any type known per se and is(are) chosen in particular from the following list of substituents, without this list exhibiting a limiting nature:

a linear or branched C$_1$ to C$_6$, preferably C$_1$ to C$_4$, alkyl group, such as methyl, ethyl, propyl, isopropyl, butyl, isobutyl, sec-butyl or tert-butyl;

a linear or branched C$_2$ to C$_6$, preferably C$_2$ to C$_4$, alkenyl or alkynyl group, such as vinyl or allyl;

a linear or branched C$_1$ to C$_6$, preferably C$_1$ to C$_4$, alkoxy or thioether group, such as methoxy, ethoxy, propoxy, isopropoxy or butoxy groups, an alkenyloxy group, preferably an allyloxy group, or a phenoxy group;

a cyclohexyl, phenyl or benzyl group;

a group or a functional group such as hydroxyl, thiol, carboxyl, ester, amide, formyl, acyl, aryl, amide, urea, isocyanate, isothiocyanate, nitrile, azide, nitro, sulfone, sulfo, halogen, pseudo-halogen or trifluoromethyl.

R¹ can also be a saturated, unsaturated or aromatic heterocyclyl radical comprising 5 or 6 atoms and comprising sulfur, oxygen and/or nitrogen as heteroatom(s). In this respect, mention may in particular be made of the pyridyl, pyrazolyl or imidazolyl groups.

Mention may in particular be made, as examples of compounds corresponding to the formula (A) and more generally to the formula R⁰—Y, of fluorobenzene, chlorobenzene, iodobenzene, bromobenzene, para-chlorotoluene, para-bromotoluene, para-bromoanisole, meta-bromoanisole, para-iodoanisole, para-cyanobromobenzene, para-cyanoiodobenzene, para-bromotrifluoromethylbenzene, para-bromophenylbenzene, 1-iodonaphthalene, para-bromo(methylcarbonyl)benzene, 3-bromopyridine, para-iodonitrobenzene, methyl ortho-iodobenzoate, 1-bromonaphthalene, para-bromomethylbenzene and 2-bromopyridine.

Mention may in particular be made, as examples of compounds corresponding to formula A and more generally to the formula $R^0$—$(Y)_2$ comprising two leaving groups, of ortho-difluorobenzene, meta-difluorobenzene, para-difluorobenzene, ortho-dichlorobenzene, meta-dichlorobenzene, para-dichlorobenzene, ortho-diiodobenzene, meta-diiodobenzene, para-diiodobenzene, ortho-dibromobenzene, meta-dibromobenzene, para-dibromobenzene, ortho-chlorofluorobenzene, ortho-iodofluorobenzene, ortho-bromofluorobenzene, meta-chlorofluorobenzene, meta-iodofluorobenzene, meta-bromofluorobenzene, meta-chlorofluorobenzene, meta-iodofluorobenzene, meta-bromomethylbenzene, para-chlorofluorobenzene, para-iodofluorobenzene, para-bromofluorobenzene, ortho-iodochlorobenzene, ortho-bromochlorobenzene, meta-iodochlorobenzene, meta-bromochlorobenzene, para-iodochlorobenzene, para-bromochlorobenzene, ortho-bromoiodobenzene, meta-bromoiodobenzene and para-bromoiodobenzene.

The aromatic compounds carrying a leaving group of formula $R^0$—$Y_m$ defined above are either commercially available or are easily accessible from known products and known procedures or procedures described in the scientific literature, the patent literature, Chemical Abstracts or the Internet.

According to the process of the invention, the aromatic compound carrying a leaving group is brought into contact with aqueous ammonia, that is to say a solution of ammonia in water, prepared according to techniques known to a person skilled in the art or directly available commercially. The aqueous ammonia solutions which can be used in the context of the invention are solutions of variable concentrations and generally of concentrations of between 1% and 30% by weight, advantageously of greater than 25%, preferably at approximately 28% aqueous ammonia solution.

In accordance with the process of the invention, aqueous ammonia is reacted with an aromatic compound carrying a leaving group in the presence of a catalytic system comprising a copper/ligand complex.

This is because it has been discovered that it is possible to carry out amination reactions of aromatic compounds, such as the reactions defined above, between aqueous ammonia and aromatic compounds carrying a leaving group, by using a catalytic system comprising a metal/ligand complex.

Copper/ligand complex is understood to mean a complex composed of copper(0), copper(I), copper(II) or copper(III) and an organic ligand, with the exclusion of copper salts.

In one embodiment, the copper/ligand complex is composed of copper(I) or copper(II) and an organic ligand, with the exclusion of copper salts.

Iron/ligand complex is understood to mean the compounds composed of iron(0), iron(I), iron(II) or iron(III) and an organic ligand, with the exclusion of iron salts.

In one embodiment, the iron/ligand complex is composed of iron(II) or iron(III) and an organic ligand, with the exclusion of iron salts.

Mention may be made, as examples of catalytic systems capable of being employed, of those comprising at least one copper/ligand or iron/ligand complex, that is to say complexes of copper with at least one ligand or of iron with at least one ligand.

The copper/ligand or iron/ligand complexes which can be used in the present invention are well known to a person skilled in the art. They are either available commercially or are easily prepared from known compounds available according to procedures known in the scientific literature, the patent literature, Chemical Abstracts or the Internet.

For example, the copper-based complexes defined above can be prepared by bringing at least one ligand into contact with metallic copper or a copper derivative (copper(0), copper(I), copper(II) or copper(III)), for example a copper halide, such as cupric or cuprous iodide, bromide or chloride, or other derivatives.

For example, the iron-based complexes defined above can be prepared by bringing at least one ligand into contact with metallic iron or an iron derivative (iron(0), iron(I), iron(II) or iron(III)), for example an iron halide, such as ferric or ferrous iodide, bromide or chloride, or other derivatives.

The complex is generally formed under an inert atmosphere, for example under nitrogen or argon, in an organic solvent medium, preferably a polar aprotic solvent, for example acetonitrile or DMF. This complexing reaction is usually carried out at a temperature of between 0° C. and 80° C., depending on the nature of the compounds brought together, and the reaction temperature is generally ambient temperature.

The complex is generally obtained in the form of a precipitate which is isolated from the reaction medium according to techniques known per se, for example by filtration, and optionally recrystallization from a solvent, advantageously identical to that used for the complexing reaction.

According to one alternative form, the metal/ligand, copper/ligand or iron/ligand, complex can be prepared in situ in the reaction medium of the reaction for the preparation of arylamines according to the invention.

The metal/ligand complexes are copper(0), copper(I), copper(II), copper(III), iron(0), iron(I), iron(II) or iron(III) complexes. In one embodiment, the ligand is selected from the group consisting of β-diketones. Mention may be made, among the ligands of β-diketone type, of those selected from the group consisting of pentane-2,4-dione (acetylacetone), 1,5-diphenylpentane-2,4-dione, 3-methylpentane-2,4-dione, 1-(N,N-dimethylamino)butane-1,3-dione, 2-acetylcyclohexanone, 2,2,6,6-tetramethylheptane-3,5-dione and 1-ethoxybutane-1,3-dione, without this list in any way constituting a limitation.

In one embodiment, the ligand is acetyl-acetonate (acac), which forms, with copper, the copper(II)/acetylacetonate complex or Cu(acac)$_2$.

The use can also be envisaged of the copper/ligand complex as defined above in combination with one or more other copper compounds, in particular those chosen from metallic copper, copper(I) or copper(II) oxides, copper(I) or copper(II) hydroxides, or organic or inorganic copper(I) or copper(II) salts.

As nonlimiting examples, such copper compounds can be selected from copper(0), copper halides (for example copper(I) iodide, copper(I) bromide, copper(II) bromide, copper(I) chloride or copper(II) chloride), copper oxides or hydroxides (for example copper(I) oxide, copper(II) oxide or copper(III) hydroxide), copper nitrates (for example copper(I) nitrate or copper(II) nitrate), copper sulfates or sulfites (for example copper(I) sulfate, copper(II) sulfate or copper(I) sulfite), or organic copper salts in which the counterion comprises at least one carbon atom (for example copper(II) carbonate, copper(I) acetate, copper(II) acetate, copper(II) trifluoromethylsulfonate, copper(I) methoxide or copper(II) methoxide).

Thus, a suitable catalytic system for the process of the present invention can advantageously be copper(II) acetylacetonate, alone or in combination with one or more other copper-based catalysts and in particular those selected from metallic copper(0) (Cu), copper(I) iodide (CuI) and copper (II) oxide (CuO).

In the present text, reference is made, above and in the continuation, to the Periodic Table of the Elements published in the Bulletin de la Société Chimique de France, No. 1 (1966).

Thus, one advantage of the process of the invention is to resort to catalysis by copper rather than palladium or nickel, that is to say a catalyst which is less toxic and which additionally is advantageous from the economic viewpoint.

According to one alternative form, the invention does not rule out the copper being combined with a small amount of another metal element denoted by M. The metal element M is selected from Groups VIII, Ib and IIb of the Periodic Table of the Elements, as defined above.

Mention may be made, as examples of metals M, of silver, palladium, cobalt, nickel, iron and/or zinc, manganese.

Use is advantageously made of a mixture comprising palladium and copper. The palladium can be introduced in the form of a finely divided metal or in the form of an inorganic derivative, such as an oxide or a hydroxide. It is possible to resort to an inorganic salt, preferably nitrate, sulfate, oxysulfate, halide, oxyhalide, silicate or carbonate, or to an organic derivative, preferably cyanite, oxalate, acetylacetonate, alkoxide, still more preferably methoxide or ethoxide, or carboxylate, still more preferably acetate.

Use may also be made of complexes, in particular chlorinated or cyanated complexes, of palladium and/or of alkali metals, preferably sodium or potassium, or of ammonium. Mention may in particular be made, as examples of compounds capable of being employed in the preparation of the catalysts of the invention, of palladium(II) bromide, palladium(II) chloride, palladium(II) iodide, palladium(II) cyanide, palladium(II) nitrate hydrate, palladium(II) oxide, palladium(II) sulfate dihydrate, palladium(II) acetate, palladium (II) propionate, palladium(II) butyrate or palladium benzoate.

Mention may be made, as specific examples of nickel derivatives, of nickel(II) halides, such as nickel(II) chloride, bromide or iodide; nickel(II) sulfate; nickel(II) carbonate; salts of organic acids comprising from 1 to 18 carbon atoms, such as, in particular, acetate or propionate; nickel(II) complexes, such as nickel(II) acetylacetonate, dibromobis(triphenylphosphine)nickel(II) or dibromobis(bipyridine)nickel (II); or nickel(0) complexes, such as bis(1,5-cyclooctadiene) nickel(0) or bis(diphenylphosphinoethane)nickel(0).

Recourse may also be made to derivatives based on iron or on zinc, generally in the form of oxide, of hydroxides or of salts, such as halides, preferably chloride, nitrates and sulfates.

The amount of the metal element M is less than molar %, preferably less than 25 molar %, advantageously less than 10 molar %, with respect to the number of moles of copper.

Still more preferably, use is made, in the process of the invention, of a catalytic system comprising solely copper, as metal, in the form of a complex with a ligand. A very particularly preferred complex is copper acetylacetonate (Cu (acac)$_2$).

The complex(es) present in the catalytic system employed in the process of the invention can optionally be supported, as is known in the field, for example on an inorganic, silica, alumina support or other supports, in particular based on metal oxides or nonmetal oxides.

The total amount of copper/ligand complex catalyst employed in the process of the invention, expressed by the molar ratio of the number of moles of complex, expressed as copper, to the number of moles of aromatic compound carrying a leaving group, generally varies between 0.001 and 1, preferably between 0.01 and 0.1.

A base is also involved in the process of the invention, the role of which is to scavenge the leaving group.

The bases suitable for the process of the invention can be characterized by their pKa, which is advantageously at least greater than or equal to 2, preferably between 4 and 30.

The pKa is defined as the ionic dissociation constant of the acid/base pair when water is used as solvent. For the choice of a base having a pKa as defined by the invention, reference may be made, inter alia, to the Handbook of Chemistry and Physics, 66th edition, pp. D-161 and D-162.

Mention may be made, among the bases which can be used, inter alia, of inorganic bases, such as carbonates, hydrogencarbonates, phosphates or hydroxides of alkali metals, preferably of sodium, of potassium or of cesium, or of alkaline earth metals, preferably of calcium, barium or magnesium.

Recourse may also be made to alkali metal hydrides, preferably sodium hydride, or to alkali metal alkoxides, preferably sodium or potassium alkoxides, and more preferably to sodium methoxide, ethoxide or tert-butoxide.

Organic bases, such as tertiary amines, are also suitable and mention may more particularly be made of triethylamine, tri(n-propyl)amine, tri(n-butyl)amine, methyldibutylamine, methyldicyclohexylamine, ethyldiisopropylamine, N,N-diethylcyclohexylamine, pyridine, 4-(dimethylamino)pyridine, N-methylpiperidine, N-ethylpiperidine, N-(n-butyl)piperidine, 1,2-dimethylpiperidine, N-methylpyrrolidine and 1,2-dimethylpyrrolidine.

The choice is preferably made, among the bases, of alkali metal carbonates, advantageously sodium carbonate, potassium carbonate and, very particularly, cesium carbonate.

The amount of base employed is such that the ratio of the number of moles of base to the number of moles of the aromatic compound carrying the leaving group preferably varies between 0.5 and 4 and is preferably equal to approximately 2.

However, the presence of a base, as indicated above, is not essential. This is because the reaction medium comprises ammonia, a basic compound which can also behave as scavenger of the leaving group. In this case, aqueous ammonia will advantageously be added in excess to the reaction medium.

The coupling reaction, in particular the amination reaction of an aromatic compound according to the invention, is generally carried out in the presence of an organic solvent. Recourse is preferably made to an organic solvent which does not react under the conditions of the reaction.

Recourse is preferably made, as types of the solvent employed in the process of the invention, to a polar organic solvent and preferably a polar aprotic organic solvent.

Nonlimiting examples of solvents which can be employed in the process of the invention are selected from:

linear or cyclic carboxamides, such as N,N-dimethylacetamide (DMAC), N,N-diethylacetamide, dimethylformamide (DMF), diethylformamide or 1-methyl-2-pyrrolidinone (NMP);

dimethyl sulfoxide (DMSO);

hexamethylphosphotriamide (HMPT);

tetramethylurea;

nitro compounds, such as nitromethane, nitroethane, 1-nitropropane, 2-nitropropane or their mixtures, or nitrobenzene;

aliphatic or aromatic nitriles, such as acetonitrile, propionitrile, butanenitrile, isobutane-nitrile, pentanenitrile, 2-methylglutaronitrile or adiponitrile;

tetramethylene sulfone (sulfolane);

organic carbonates, such as dimethyl carbonate, diisopropyl carbonate or di(n-butyl) carbonate;

alkyl esters, such as ethyl acetate or isopropyl acetate;

halogenated or nonhalogenated aromatic hydrocarbons, such as chlorobenzene or toluene;

ketones, such as acetone, methyl ethyl ketone, methyl isobutyl ketone, cyclopentanone or cyclohexanone;

nitrogenous heterocycles, such as pyridine, picoline and quinolines.

Use may also be made of a mixture of two or more solvents chosen in particular from those listed above.

The preferred solvents are carboxamides, such as DMF, acetonitrile, DMSO, NMP and DMAC, quite preferably DMF and/or acetonitrile.

The amount of organic solvent employed is determined as a function of the nature of the organic solvent chosen. It is determined in such a way that the concentration of the compound carrying the leaving group in the organic solvent is preferably between 1% and 40% by weight.

According to another aspect, the amount of solvent(s) introduced into the reaction medium is such that the amount of solvent/total amount of water (including the water of the aqueous ammonia solution) ratio by weight is generally between 1 and 50, preferably between 3 and 30.

As indicated above, the reaction according to the invention employs an aqueous ammonia solution. The solvent of the reaction is advantageously soluble in water, in particular the water of the aqueous ammonia solution. In an alternative form, the solvent can be added to the reaction medium as a mixture with an additional amount of water.

According to another alternative form, the nucleophilic compound and/or the compound carrying the leaving group can be used as solvent(s) of the reaction, in which case it is not necessary to add an additional solvent to the reaction medium.

The amount of the aromatic compound carrying a leaving group employed is generally expressed with respect to the amount of ammonia (number of moles of $NH_3$) and can vary within wide proportions; generally, it is in the vicinity of stoichiometry.

Thus, the ratio of the number of moles of the aromatic compound carrying the leaving group to the number of moles of ammonia (number of moles of $NH_3$) generally varies between 0.01 and 2.0, preferably between 0.05 and 1.0 and more preferably still between 0.1 and 0.3.

Another advantage of the process of the invention is that of carrying out the reaction at moderate temperature.

The amination reaction of the aromatic compound according to the process of the invention is generally carried out at a temperature which is advantageously situated between 20° C. and 200° C., preferably between 30° C. and 130° C. and more preferably still between 40° C. and 110° C.

Said reaction is generally carried out at atmospheric pressure or under a slight excess pressure but higher pressures, which can reach, for example, 10 bar, can also be used. Very good yields and very good selectivities have been obtained at pressures of less than 1.38 bar.

In addition, the reaction according to the invention can be carried out without requiring an inert atmosphere. However, said reaction can be carried out under nitrogen, argon or other inert gas commonly used in organic synthesis.

The reaction is simple to carry out from a practical viewpoint.

Another advantage is to be able to use a wide range of aromatic compounds carrying a leaving group, not only iodides but also bromides, chlorides or triflates, in particular aryl iodides, aryl bromides, aryl chlorides or aryl triflates.

The order of use of the reactants is not critical. Preferably, the copper/ligand complex catalytic system, aqueous ammonia, the organic compound carrying the leaving group and optionally the base and the organic solvent are charged. The reaction medium is then brought to the desired temperature.

As mentioned above, it is possible, in an alternative form, to introduce the copper and at least one ligand in order to form the copper/ligand complex in situ.

The progress of reaction is monitored by following the disappearance of the aromatic compound carrying the leaving group. At the end of the reaction, a product of the $R^O$—$NH_2$ type is obtained, Fe being as defined above.

The duration of the reaction varies according to several parameters, including amounts and natures of the reactants, catalysts and solvents employed. In addition, the duration of the reaction depends on the temperature at which it is carried out. Generally, the reaction time can vary from a few minutes to several hours, indeed even several tens of hours, more generally between 1 hour and 20 hours.

The compound obtained is finally recovered according to the conventional techniques used, in particular by crystallization from an organic solvent, when the product obtained is a solid.

Mention may in particular be made, as more specific examples of such organic solvents which can be used in the crystallization stage, of aliphatic or aromatic and halogenated or nonhalogenated hydrocarbons, carboxamides and nitriles. Mention may in particular be made of cyclohexane, toluene, dimethyl-formamide or acetonitrile.

As another advantage, the process according to the invention thus makes it possible to easily obtain arylamines $R^O$—$NH_2$ from aromatic precursors carrying a leaving group $R^O$—Y, where $R^O$ and Y are as defined above, in particular in a single step (one pot reaction).

In particular, the process of the invention makes it possible to selectively obtain aniline in a single step, starting from a phenyl halide and from aqueous ammonia, with good yields, at a temperature of 90° C. at atmospheric pressure, in the presence of a catalytic system comprising a Cu/ligand complex and of a base, in a water/DMF solvent medium.

The invention is now illustrated by means of the following examples, which do not exhibit any limiting nature.

EXAMPLES

Example A

Synthesis of 1-aminonaphthalene

The copper/acetylacetonate complex ([Cu(acac)$_2$]; 52 mg; 0.2 mmol), acetylacetone (82 µl, 0.8 mmol), 1-iodonaphthalene (508 mg; 2 mmol) and cesium carbonate (Cs$_2$CO$_3$; 978 mg; 3.0 mmol) are introduced into a Schlenk tube or a Radley tube (purged with nitrogen and filled with nitrogen beforehand).

Dimethylformamide (DMF; 4 ml) is then added under nitrogen, followed by 28% (by weight) aqueous ammonia (600 µl). The tube is sealed under nitrogen and the mixture is heated to 90° C. and stirred for 24 hours. After cooling to ambient temperature, the mixture is diluted with dichloromethane and then washed with water. The aqueous phase is extracted five times with dichloromethane. The organic phases are combined, dried over sodium sulfate (Na$_2$SO$_4$) and then concentrated to provide the crude product.

This crude product is purified by chromatography on silica gel (eluent cyclohexane/ethyl acetate 9/1) to provide 1-aminonaphthalene in the form of a solid.

Example B

Synthesis of 4-aminobenzonitrile

The copper/acetate (Cu(OAc)$_2$; 36 mg; 0.2 mmol), 3-methyl-2,4-pentanedione (156 µl, 1.2 mmol), 4-iodo-benzonitrile (458 mg; 2 mmol) and cesium carbonate (Cs$_2$CO$_3$; 978 mg; 3.0 mmol) are introduced into a Schlenk tube or a Radley tube (purged with nitrogen and filled with nitrogen beforehand).

Dimethylformamide (DMF; 4 ml) is then added under nitrogen, followed by 28% (by weight) aqueous ammonia (600 µl). The tube is sealed under nitrogen and the mixture is heated to 90° C. and stirred for 24 hours. After cooling to ambient temperature, the mixture is diluted with dichloromethane and then washed with water. The aqueous phase is extracted five times with dichloromethane. The organic phases are combined, dried over sodium sulfate (Na$_2$SO$_4$) and then concentrated to provide the crude product.

This crude product is purified by chromatography on silica gel (eluent cyclohexane/ethyl acetate 9/1) to provide 4-aminobenzonitrile in the form of a solid.

Example C

Synthesis of 3-anisidine

The copper/acetylacetone complex ([Cu(acac)$_2$]; 52 mg; 0.2 mmol), acetylacetone (82 µl, 0.8 mmol), 3-bromoanisole (374 mg; 2 mmol) and cesium carbonate (Cs$_2$CO$_3$; 978 mg; 3.0 mmol) are introduced into a Schlenk tube or a Radley tube (purged with nitrogen and filled with nitrogen beforehand).

Dimethylformamide (DMF; 4 ml) is then added under nitrogen, followed by 28% (by weight) aqueous ammonia (600 µl). The tube is sealed under nitrogen and the mixture is heated to 90° C. and stirred for 24 hours. After cooling to ambient temperature, the mixture is diluted with dichloromethane and then washed with water. The aqueous phase is extracted five times with dichloromethane. The organic phases are combined, dried over sodium sulfate (Na$_2$SO$_4$) and then concentrated to provide the crude product.

This crude product is purified by chromatography on silica gel (eluent cyclohexane/ethyl acetate 9/1) to provide 3-anisidine in the form of an oil.

Example D

Influence of the Compound Carrying the Leaving Group

In order to test the scope of the amination reaction, various tests were carried out according to the same procedures as those described above, starting from different aryl halides carrying either electron-withdrawing or electron-donating substituents.

The results are presented in table 1.

TABLE 1

Reactions with various aromatic precursors

R—Ar—X + NH$_3$·H$_2$O $\xrightarrow[\text{1-2.5 equiv. Cs}_2\text{CO}_3]{\substack{\text{0.1 equiv. Cu(acac)}_2 \\ \text{0.4 equiv. L} \\ \text{DMF, 90° C., 24 h}}}$ R—Ar—NH$_2$

| N° | ArX | ArNH$_2$ | Yield[‡] (%) |
|---|---|---|---|
| D1 | 1-iodonaphthalene | 1-aminonaphthalene | 90 |
| D2 | MeO—C$_6$H$_4$—I | MeO—C$_6$H$_4$—NH$_2$ | 80 |
| D3 | NC—C$_6$H$_4$—I | NC—C$_6$H$_4$—NH$_2$ | 93**, 99[†], 97* |
| D4 | O$_2$N—C$_6$H$_4$—I | O$_2$N—C$_6$H$_4$—NH$_2$ | 63 |
| D5 | 2-iodo-C$_6$H$_4$—COOMe | 2-amino-C$_6$H$_4$—COOMe | 23 |

TABLE 1-continued

Reactions with various aromatic precursors

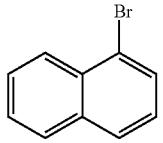 [SMILES: Ic1cccc2ccccc12]

| N° | ArX | ArNH$_2$ | Yield[‡] (%) |
|---|---|---|---|
| D6 | PhBr | PhNH$_2$ | 78 |
| D7 | 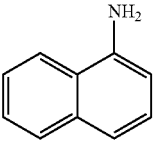 | 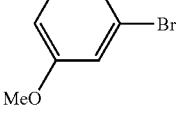 | 88 |
| D8 | 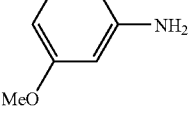 | 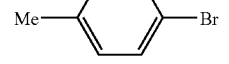 | 85 |
| D9 | 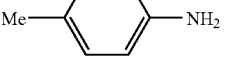 | 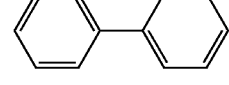 | 65, 79*** |
| D10 | 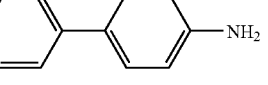 | 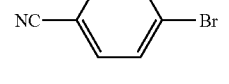 | 90, 98[††] |
| D11 | 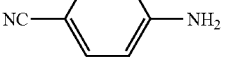 | 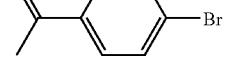 | 92, (82 * and **) |
| D12 | 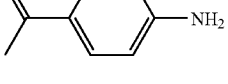 | 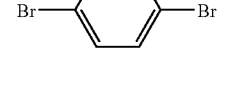 | 92, 84** |
| D13 | 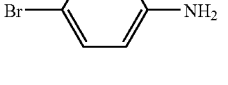 | 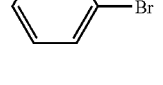 | 41[†††] |
| D14 | 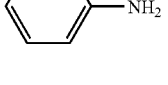 | 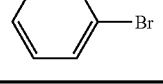 | 84 |
| D15 | 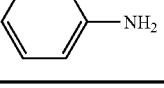 | | 82 |

The yields are the isolated yields. Unless otherwise indicated, 2,4-pentanedione is used as ligand.
[‡]With 3-methyl-2,4-pentanedione or 2,2,6,6-tetramethyl-3,5-heptanedione used as ligand.
*Reaction carried out at 70° C.
**Reaction carried out at 60° C.
***Reaction time 36 h.
[††]Carried out with 2,2,6,6-tetramethyl-3,5-heptanedione.
[†††]Formation of the double substitution product paraaminoaniline 42%.

Example E

Influence of the Ligand

In order to test the influence of the nature of the ligands on the amination reaction, various tests were carried out starting from 4-bromobiphenyl in the presence of copper complexes with different ligands.

The results are presented in Table 2.

Example F

Influence of the Source of the Copper and of the Solvents

In order to test the influence of the source of copper and of the solvents, various tests were carried out starting from 4-bromobiphenyl of Cu(acac)$_2$ complex in the presence of various copper salts and of various solvents.

TABLE 2

Reactions in the presence of copper complexes with different ligands

Ph—C$_6$H$_4$—Br + NH$_3$·H$_2$O → (0.1 equiv. CuI/L cat., 1-2.5 equiv. Cs$_2$CO$_3$, DMF, 90° C., 15 h) → Ph—C$_6$H$_4$—NH$_2$

| N° | Ligands L | Yield[‡] (%) | Selectivity[†] |
|---|---|---|---|
| E1 | pentane-2,4-dione (acac) | 76 | 92 |
| E2 | 1,3-diphenylpropane-1,3-dione | 24 | 92 |
| E3 | 3-methylpentane-2,4-dione | 7 | — |
| E4 | N,N-dimethyl-3-oxobutanamide | 29 | 91 |
| E5 | 2-acetylcyclohexanone | 35 | 99 |
| E6 | 2,2,6,6-tetramethylheptane-3,5-dione | 79 | 99 |
| E7 | ethyl acetoacetate | 7 | — |
| E8 | 2'-hydroxyacetophenone | 0 | — |

[‡]L (0.6 eq) and commercial 28% aqueous NH$_3$ (5 eq) were used. Yield determined using 1,3-dimethoxybenzene as standard.
[†]Selectivity/C-C coupling between L and 4-bromobiphenyl.

TABLE 3

Reactions in the presence of various copper salts and solvents

Ph—C6H4—Br + NH3·H2O → Ph—C6H4—NH2

(0.1 equiv. [Cu], 1-2.5 equiv. Cs2CO3, solvent, 90° C., 15 h; Ligand 1 = 2,2,6,6-tetramethyl-3,5-heptanedione)

| No. | [Cu], 0.1 eq. | Ligand 1 (eq.) | Solvent | Yield[a] [%] |
|---|---|---|---|---|
| F1 | — | 0.6 | DMF | 0 |
| F2 | CuI | — | DMF | 0[b] |
| F3 | CuI | 0.6 | DMF | 2[c] |
| F4 | CuI | 0.6 | DMF | 76 |
| F5 | Cu | 0.6 | DMF | 68 |
| F6 | CuO | 0.6 | DMF | 79 |
| F7 | Cu(OAc)$_2$ | 0.6 | DMF | 73 |
| F8 | Cu$_2$O | 0.6 | DMF | 63 |
| F9 | Cu(acac)$_2$ | — | DMF | 23 |
| F10 | Cu(acac)$_2$ | 0.4 | DMF | 76 |
| F11 | Cu(acac)$_2$ | 0.4 | DMSO | 18 |
| F12 | Cu(acac)$_2$ | 0.4 | CH$_3$CN | 34 |
| F13 | Cu(acac)$_2$ | 0.4 | NMP | 50 |
| F14 | Cu(acac)$_2$ | 0.4 | H$_2$O | 0 |
| F15 | Cu(acac)$_2$ | 0.4 | DMF | 6[d] |
| F16 | Cu(acac)$_2$ | 0.4 | DMF | 45[e] |
| F17 | Cu(acac)$_2$ | 0.4 | DMF | 45[f] |
| F18 | Cu(acac)$_2$ | 0.4 | DMF | 93[g], 20[h] |

[a]Yield determined using 1,3-dimethoxybenzene as internal standard.
[b]Same result at 140° C.
[c]Without base.
[d]DMF presaturated with gaseous ammonia.
[e]Addition of 0.5 eq. of NBu$_4^t$Br$^-$.
[f]K$_2$CO$_3$ was used instead of Cs$_2$CO$_3$.
[g]Reaction time 24 h.
[h]Reaction time 24 h, 3% of Cu(acac)$_2$ was used.

Example G

Synthesis of Aniline Catalyzed with Iron

The iron/acetylacetonate complex ([Fe(acac)$_3$]; 70 mg; 0.2 mmol), 2,2,6,6-tetramethyl-3,5-heptanedione (166 μl; 0.8 mmol), iodobenzene (204 mg; 1 mmol) and cesium carbonate (Cs$_2$CO$_3$; 489 mg; 1.5 mmol) are introduced into a Schlenk tube or a Radley tube (purged with nitrogen and filled with nitrogen beforehand).

Dimethylformamide (DMF; 2 ml) is then added under nitrogen, followed by 28% (by weight) aqueous ammonia (300 μl). The tube is sealed under nitrogen and the mixture is heated to 140° C. and stirred for 24 hours. After cooling to ambient temperature, the mixture is diluted with dichloromethane and then washed with water. The aqueous phase is extracted five times with dichloromethane. The organic phases are combined, dried over sodium sulfate (Na$_2$SO$_4$) and then concentrated to provide the crude product.

This crude product is purified by chromatography on silica gel (eluent cyclohexane/ethyl acetate 9/1) to provide the aniline (20%-30%) in the form of an oil.

The present invention thus provides a general process which is easy to carry out, economic and effective for converting aryl halides to aniline derivatives, said process comprising only a single step. Good yield and good selectivities, allied to a great variety of possible substituents, render this process entirely profitable and capable of industrial application, in particular in the field of organic synthesis.

The relatively low costs, both of the aqueous ammonia and of the catalytic copper, render the process according to the present invention readily adaptable and profitable economically for large-scale industrial production of arylamines (aniline and derivatives), in particular where questions of safety and of the environment play a dominating role.

What is claimed is:
1. A process for the preparation of arylamines of formula R$^0$—(NH$_2$)$_n$, where R$^0$ is an aromatic radical and n is between 1 and 3, said process comprising the following steps:
 a) preparation of a reaction medium comprising:
  1) an aromatic compound carrying at least one leaving group, of formula R$^0$—Y$_m$, in which R$^0$ is an aromatic radical and Y is a leaving group, m being between 1 and 3;
  2) an aqueous ammonia solution;
  3) a catalytic system comprising a complex selected from the group consisting of Cu/β-diketone and Fe/β-diketone;
  4) optionally a base; and
  5) optionally a solvent;
 b) heating said reaction medium to a temperature of between 20° C. and 200° C.;
 c) carrying out the reaction; and
 d) extracting and isolating the arylamine R$^0$—(NH$_2$)$_n$ formed,
wherein the R$^0$ radical of the aromatic compound carrying a leaving group is a monocyclic or polycyclic and aromatic or heteroaromatic radical comprising from 2 to 20 atoms.

2. The process as claimed in claim 1, in which the leaving group Y is a halogen atom or a sulfonic ester group of formula —OSO$_2$—R$^e$, in which R$^e$ is a linear or branched alkyl radical having from 1 to 4 carbon atoms, a phenyl or tolyl group or a trifluoromethyl group.

3. The process as claimed in claim 1, in which the aromatic compound carrying a leaving group R$^O$—Y has the formula (A):

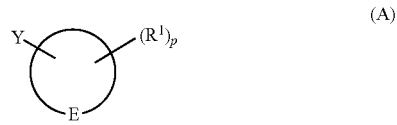

in which:
E symbolizes the residue of a ring forming all or part of a carbocyclic and/or heterocyclic system which is aromatic and monocyclic or polycyclic;
R$^1$, which are identical or different, are substituents on the ring;
Y is a leaving group as defined above; and
p is the number of substituents on the ring.

4. The process as claimed in claim 3, in which E is the residue of an aromatic carbocycle or of an aromatic heterocycle selected from benzene, naphthalene, 1,2,3,4-tetrahydronaphthalene, furan, pyridine, benzofuran, benzopyridine, methylenedioxybenzene, 1,8-naphthylpyridine and 5,6,7,8-tetrahydroquinoline.

5. The process as claimed in claim 1, in which the aromatic compound carrying a leaving group is selected from fluorobenzene, chlorobenzene, iodobenzene, bromobenzene, para-chlorotoluene, para-bromotoluene, para-bromoanisole, meta-bromoanisole, para-iodoanisole, para-cyanobromobenzene, para-cyanoiodobenzene, para-bromotrifluoromethylbenzene, para-bromophenylbenzene, 1-iodonaphthalene, para-bromo(methylcarbonyl)benzene, 3-bromopyridine, para-iodonitrobenzene, methyl ortho-iodobenzoate, 1-bromonaphthalene, para-bromomethylbenzene and 2-bromopyridine.

6. The process as claimed in claim 1, in which the aromatic compound carrying two leaving groups is selected from ortho-difluorobenzene, meta-difluorobenzene, para-difluorobenzene, ortho-dichlorobenzene, meta-dichlorobenzene, para-dichlorobenzene, ortho-diiodobenzene, meta-diiodobenzene, para-diiodobenzene, ortho-dibromobenzene, meta-dibromobenzene, para-dibromobenzene, ortho-chlorofluorobenzene, ortho-iodofluorobenzene, ortho-bromofluoromethylbenzene, meta-chlorofluorobenzene, meta-iodofluorobenzene, meta-bromofluorobenzene, meta-chlorofluorobenzene, meta-iodofluorobenzene, meta-bromobenzene, para-chlorofluoro-benzene, para-iodofluorobenzene, para-bromofluorobenzene, ortho-iodochlorobenzene, ortho-bromochlorobenzene, meta-iodochlorobenzene, meta-bromochlorobenzene, para-iodochlorobenzene, para-bromochlorobenzene, ortho-bromoiodobenzene, meta-bromoiodobenzene and para-bromoiodobenzene.

7. The process as claimed in claim 1, in which the copper/ligand complex of the catalytic system is a complex of copper (I) or of copper(II) with a ligand of β-diketone type selected from pentane-2,4-dione (acetylacetone), 1,5-diphenylpentane-2,4-dione, 3-methylpentane-2,4-dione, 1-(N,N-dimethylamino)-butane-1,3-dione, 2-acetylcyclohexanone, 2,2,6,6-tetramethylheptane-3,5-dione and 1-ethoxybutane-1,3-dione.

8. The process as claimed in claim 1, in which the catalytic system is the copper acetylacetonate (Cu(acac)$_2$) complex.

9. The process as claimed in claim 1, in which the molar ratio of the number of moles of complex, expressed as copper, to the number of moles of aromatic compound carrying a leaving group varies between 0.001 and 1.

10. The process as claimed in claim 1, in which the base present in the reaction medium has a pKa at least greater than or equal to 2.

11. The process as claimed in claim 1, in which the base is selected from carbonates, hydrogencarbonates, phosphates or hydroxides of alkali metals, or of alkaline earth metals.

12. The process as claimed in claim 1, in which the amount of base employed is such that the ratio of the number of moles of base to the number of moles of the aromatic compound carrying the leaving group is between 0.5 and 4.

13. The process as claimed in claim 1, in which the reaction is carried out in the presence of a polar aprotic organic solvent selected from the group consisting of:
linear or cyclic carboxamides, such as N,N-dimethylacetamide (DMAC), N,N-diethylacetamide, dimethylformamide (DMF), diethylformamide or 1-methyl-2-pyrrolidinone (NMP);
dimethyl sulfoxide (DMSO);
hexamethylphosphortriamide (HMPT);
tetramethylurea;
nitro compounds, or nitrobenzene;
aliphatic or aromatic nitriles,
tetramethylene sulfone (sulfolane);
organic carbonates,
alkyl esters,
halogenated or nonhalogenated aromatic hydrocarbons;
ketones, and
nitrogenous heterocycles.

14. The process as claimed in claim 12, in which the solvent is selected from the group consisting of dimethylformamide and acetonitrile.

15. The process as claimed in claim 1, in which the ratio of the number of moles of the aromatic compound carrying the leaving group to the number of moles of ammonia (number of moles of NH$_3$) is between 0.01 and 2.0.

16. The process as claimed in claim 1, in which the reaction is carried out at a temperature of between 20° C. and 200° C.

17. The process as claimed in claim 9, which is carried out in the presence of a polar organic solvent.

18. The process as claimed in claim 1, in which the reaction is carried out at atmospheric pressure.

19. The process as claimed in claim 1, for the preparation of aniline in a single step, starting from a phenyl halide and from aqueous ammonia, at a temperature of 90° C., in the presence of a catalytic system comprising a Cu/ligand complex and of a base, in a water/DMF solvent medium.

20. The process as claimed in claim 1, in which the reaction is carried out at atmospheric pressure.

21. The process as claimed in claim 9 wherein the molar ratio of the number of moles of complex, expressed as copper, to the number of moles of aromatic compound carrying a leaving group varies between 0.01 and 0.1.

22. The process as claimed in claim 11, in which the base present in the reaction medium has a pKa of between 4 and 30.

23. The process as claimed in claim 11, in which the base is selected from the group consisting of carbonates, hydrogen carbonates, phosphates and hydroxides of sodium, potassium, cesium, calcium, barium and magnesium.

24. The process as claimed in claim 12, in which the amount of base employed is such that the ratio of the number of moles of base to the number of moles of the aromatic compound carrying the leaving group is approximately 2.

25. The process as claimed in claim 13, wherein the nitro compound is selected from the group consisting of nitromethane, nitroethane, 1-nitropropane, 2-nitropropane and mixtures thereof.

26. The process as claimed in claim 13, wherein the aromatic nitrile compound is selected from the group consisting of acetonitrile, propionitrile, butanenitrile, isobutanenitrile, pentanenitrile, 2-methylglutaronitrile and adiponitrile.

27. The process as claimed in claim 13, wherein the organic carbonate is selected from the group consisting of dimethyl carbonate, diisopropyl carbonate and di(n-butyl) carbonate.

28. The process as claimed in claim 13, wherein the alkyl ester is selected from the group consisting of ethyl acetate and isopropyl acetate.

29. The process as claimed in claim 13, wherein the aromatic hydrocarbon is selected from the group consisting of chlorobenzene and toluene.

30. The process as claimed in claim 13, wherein the ketone is selected from the group consisting of acetone, methyl ethyl ketone, methyl isobutyl ketone, cyclopentanone and cyclohexanone.

31. The process as claimed in claim 13, wherein the nitrogenous heterocycle is selected from the group consisting of pyridine, picoline and quinolines.

32. The process as claimed in claim 15 in which the ratio of the number of moles of the aromatic compound carrying the leaving group to the number of moles of ammonia (number of moles of $NH_3$) is between 0.05 and 1.

33. The process as claimed in claim 15 in which the ratio of the number of moles of the aromatic compound carrying the leaving group to the number of moles of ammonia (number of moles of $NH_3$) is between 0.1 and 0.3.

34. The process as claimed in claim 16, in which the reaction is carried out at a temperature of between 30° C. and 130° C.

35. The process as claimed in claim 16, in which the reaction is carried out at a temperature of between 40° C. and 110° C.

36. The process as claimed in claim 17, wherein the polar organic solvent is a polar aprotic organic solvent.

* * * * *